United States Patent
Gourley

(10) Patent No.: US 6,884,624 B1
(45) Date of Patent: Apr. 26, 2005

(54) METHOD FOR MEASURING THE RATE OF CELL REPRODUCTION BY ANALYSIS OF NANOLITER CELL SAMPLES

(75) Inventor: Paul L. Gourley, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 0 days.

(21) Appl. No.: 09/553,978

(22) Filed: Apr. 20, 2000

(51) Int. Cl.$^7$ .................... G01N 33/483; G01N 21/17; G01N 21/41; G01J 3/30; G01J 3/44
(52) U.S. Cl. ................ 436/63; 436/164; 356/246; 356/301; 356/318; 356/436; 356/440; 356/441
(58) Field of Search .................... 436/63, 164, 64; 356/246, 301, 318, 436, 440, 441; 435/4

(56) References Cited

FOREIGN PATENT DOCUMENTS

EP       798386    *   3/1997

OTHER PUBLICATIONS

The abstract of Uhal et al (Aerican Respiratory Disease, 1991,vol. 143, No. 4, part 2, p. A301).*
Luther et al (Cytometry, 1996, vol. 23, pp. 272–278).*
Meissner et al, SPIE, 1995, vol. 2399, pp. 561–570.*
Gourley, Nature Medicine, 1996, vol. 2, pp. 942–944.*
Gourley, Optics and Photonics News, 1997, vol. 8, pp. 31–36.*
Gourley, Sandia National Laboratories Technical Report, 1997 (SAND97–1988), pp. 1–26.*

* cited by examiner

*Primary Examiner*—Karen A. Canella
(74) *Attorney, Agent, or Firm*—Carol I. Ashby

(57) ABSTRACT

A method of detecting cancer using a laser biocavity having a semiconductor laser including a microchannel through which cells in fluid traverse, comprising determining the laser wavelength of the laser biocavity with only fluid in the microchannel; determining the wavelength shift of the biocavity when each cell passes through the microchannel; and determining the percentage of cells in G2 phase from the wavelength shift of the cells; wherein an increased percentage of G2 phase cells is an indication of cancer.

3 Claims, 7 Drawing Sheets

METHOD FOR MEASURING THE RATE OF CELL REPRODUCTION BY ANALYSIS OF NANOLITER CELL SAMPLES

The United States Government has rights in this invention pursuant to Department of Energy Contract No. DE-AC04-95AL85000 with Sandia Corporation.

BACKGROUND OF THE INVENTION

How cancer develops is now understood. As described by Robert Weinberg, "How Cancer Arises", *Scientific American*, September 1996, the normal, healthy human body has about 30 trillion cells which live in a complex interdependent body. The nucleus of each cell includes chromosomes having DNA molecules that contain genes. Each gene specifies a sequence of amino acids that must be linked together to make a particular protein; this protein then carries out the work of the gene. When a gene is switched on, the cell responds by synthesizing the encoded protein. Mutations in a gene can perturb a cell by changing the amounts or activities of the protein product.

Normal cells replicate only when certain biochemical conditions, internal and external to the cell, are met. The cells of a tumor are now known to descend from a single cell that begins a program of uncontrolled reproduction because of an accumulation of successive mutations, usually occurring over a long time, in specific classes of genes within the cell.

Two gene classes are instrumental in triggering cancer. Proto-oncogenes encourage cell growth, and tumor suppressor genes inhibit it. When mutated, proto-oncogenes can drive excessive cell multiplication. If, in addition, the tumor suppressor genes are mutated or turned off by other cell abnormalities, the cell loses the ability to prevent runaway growth.

Recently, biomedical science has determined that stimulatory and inhibitory pathways in a cell are carefully regulated by a complex set of processes that occur in during a cell cycle. In a normal cell, the cycle integrates the mixture of growth-regulating signals and decides whether the cell should pass through a life cycle as set forth in FIG. 1.

The life cycle is composed of four stages: In the G1 (gap 1) phase, the cell increases in size and prepares to copy its DNA. This copying occurs in the following S (synthesis) stage which enables the cell to duplicate its complement of chromosomes. After synthesis, a second gap period, G2, occurs during which the cell prepares for mitosis (M), the time when the enlarged parent cell divides in half to produce two daughter cells, each with a complete set of chromosomes. The new daughter cells immediately enter G1 and may go through the complete cycle or enter the G0 phase where cycling stops.

The difficulty in detecting cancer arises from the subtle onset of the disease in a single cell embedded in a host organ comprising billions of cells. Pathologists routinely rely on microscopic examination of cell morphology using methods that originated over a hundred years ago. These staining methods are labor-intensive, time-consuming, and frequently in error. New micro-analytical methods for high speed (real time) automated screening of tissues and cells are critical to advancing pathology and hold the potential for improving diagnosis and treatment of cancer patients.

Novel technologies to assess these diseases in their early development are crucial to effect a successful treatment and recovery. Promising techniques under investigation include non-invasive but expensive magnetic resonance imaging, inexpensive ultrasound imagining of organs or organ linings, or minimally invasive sampling of minute body tissues or fluids in microdevices. The resolution of MRI imaging is currently in the range of hundreds of microns and limited by the strength of the magnetic field and its gradient. Ultrasound resolution is limited by the wavelength of sound, and is similarly limited to hundreds of microns. Optical and Laser-based spectroscopies and imaging are inherently higher resolution, being limited only by the optical diffraction of light to hundreds of nanometers. Nanoscopic tools like the near-field optical scanning microscope push the resolution to tens of nanometers (the size of protein molecule) and are limited by fiber optic tip microfabrication techniques.

Another technique that holds promise for detection of cellular changes is the laser biocavity as disclosed in the aforementioned U.S. patent application Ser. No. 09/489,247 and related patent application Ser. No. 09/221,331, both by Paul L. Gourley, and U.S. Pat. No. 5,793,485 by Paul L. Gourley et al. The disclosure of each of these references is incorporated herein by reference thereto.

As shown in FIG. 2, the invention described in the aforementioned references incorporates a glass chip with a semiconductor laser, the chip having input and output reservoirs (on either sides of the figure) to store a small quantity of material to be tested, and a plurality of channels having a cross-sectional area on the same order of magnitude as a blood cell. A vacuum is applied to the output reservoir to pull material through the channels where it forms part of the optical path of the laser, as shown, enabling high throughput analyses of flowing biofluids.

The semiconductor nanolaser is the enabling component of this microanalysis system because of its ability to emit coherent, intense light from a small aperture compatible with the dimensions of a human cell. By permitting fluid flow through surface-emitting semiconductor geometry, there is provided a means for high throughput screening of cells, particulates and fluid analytes in a sensitive microdevice. As these fluids flow through these channels, their components will alter the emitted lasing spectrum. The spectral shifts in the lasing frequencies can then be used to measure changes in the cells.

Most importantly, cells can be analyzed in their physiologic condition as removed from the body. There are no time delays or difficulties associated with tagging cells with stains or fluorescent markers. Thus, the usual time delay of tissue pathology under the microscope is eliminated. And, the lasing technique has been found to detect subtle changes in cellular compositions that are orders of magnitude smaller than can be observed by standard optical microscopy. In addition, this device does not alter or manipulate the cellular components, thus allowing for direct observations of nuclear and cellular events.

The applications of such a portable biological sensing device are far-reaching. One potential surgical application of this biocavity laser is a "smart scalpel," for online flow cytometry in the operating room. Conventional flow cytometers tend to be large, expensive instruments that require highly trained personnel for tagging the cells and operating the instrument. A portable cytometer system designed for an operating room setting could analyze minute volumes of cells and improve the success rate of tumor resection. Such a system could decrease costs and improve patient survival rates by avoiding tumor regrowth and subsequent surgeries. To achieve this capability it is necessary to understand the basic operation of the laser and its ability to detect biologically relevant events.

SUMMARY OF THE INVENTION

It is an object of this invention to detect cancer from a very small sample of cells.

It is another object of the invention to detect cancer by detecting a higher incidence of cell division than normal in a small sample of cells.

To achieve the foregoing and other objects, and in accordance with the purpose of the present invention, as embodied and broadly described herein, the present invention may comprise a method of detecting cancer using a laser biocavity having a semiconductor laser including a microchannel through which cells in fluid traverse. The method of the invention includes the steps of determining the laser wavelength of the laser biocavity with only fluid in the microchannel; determining the wavelength shift of the biocavity when each cell passes through the microchannel; and determining the percentage of cells in G2 phase from the wavelength shift of the cells; wherein an increased percentage of G2 phase cells is an indication of cancer.

Additional objects, advantages, and novel features of the invention will become apparent to those skilled in the art upon examination of the following description or may be learned by practice of the invention. The objects and advantages of the invention may be realized and attained as particularly pointed out in the appended claims.

BRIEF DESCRIPTION OF THE DRAWINGS

The accompanying drawings, which are incorporated in and form part of the specification, illustrate an embodiment of the present invention and, together with the description, serve to explain the principles of the invention.

DETAILED DESCRIPTION OF THE INVENTION

Figure 1:
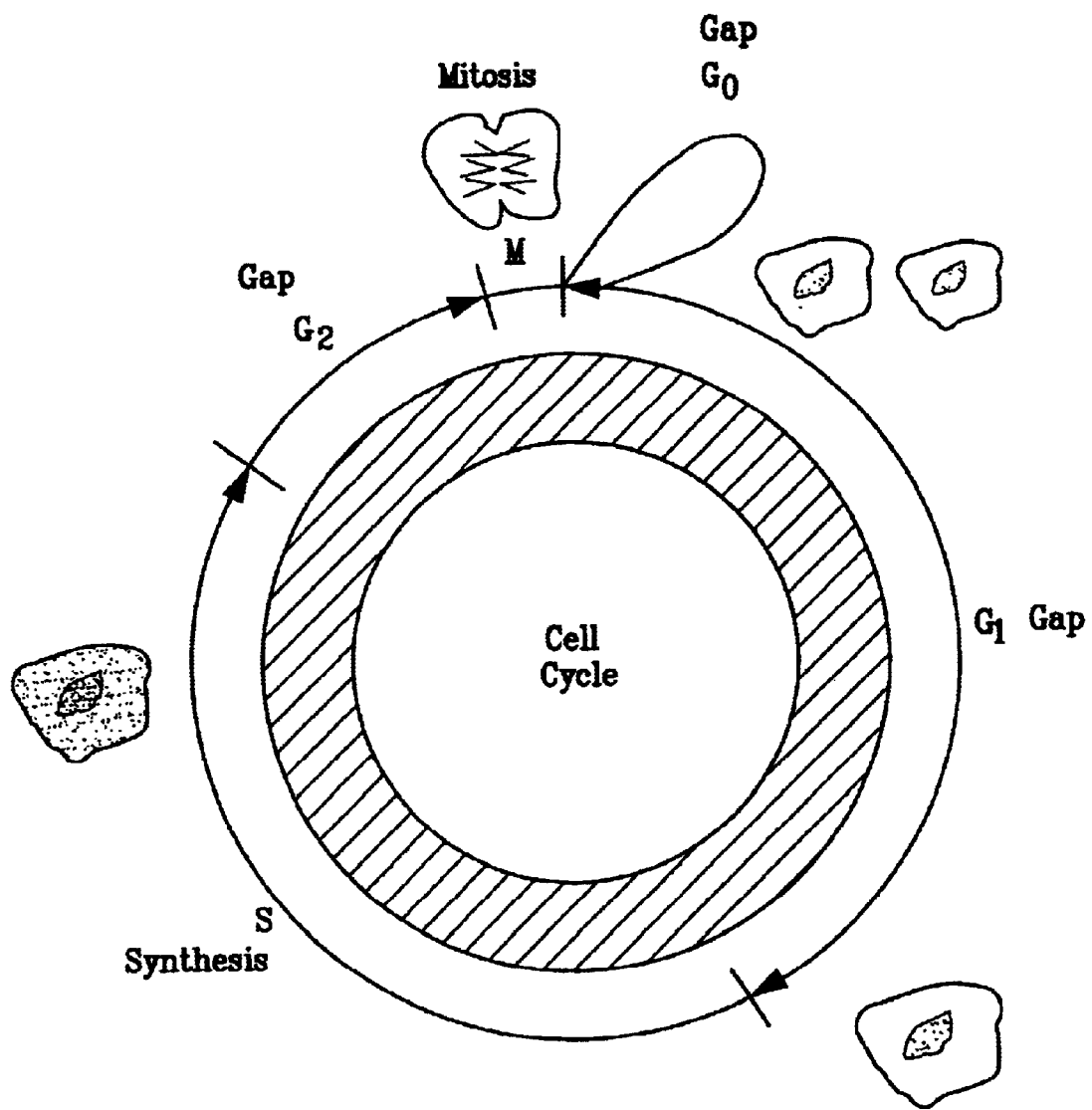
FIG. 1 shows a representation of a cell cycle.

The laser spectrum of a biocavity provides a quantitative measure of total biomolecular concentration in the cell. This measurement can be explained as follows. Typical mammalian cells are composed of water (70%), proteins (18%), lipids (S %), metabolites (3%), sugars (2%), and RNA/DNA (1–2%). Simpler molecules like $H_2O$ and sugars comprise chemical bonds that have weaker dipole oscillator strengths in the UV absorption spectrum and contribute less to the refractive index in the spectral region 850 nm where the laser operates. On the other hand, more complex molecules like protein and RNA/DNA comprise many carbon-carbon and carbon-nitrogen double bonds and have strong oscillator strengths in the UV absorption spectrum. These optical absorptions give rise to strong enhancements of the refractive index at longer wavelengths. Since the proteins are the most abundant complex molecule in the cell, and since the complex molecules contribute most strongly to the refractive index, the lasing spectrum is most sensitive to the protein content of the cell.

When a liquid is flowed through the laser microcavity, optical resonance occurs when the roundtrip light path is an integral number of light wavelengths. These resonance conditions appear as sharp peaks in the emission spectrum of the laser. When a biomolecular concentration such as a cell is placed in the microcavity, the resonance peaks are shifted to longer wavelengths and can be precisely measured with a spectrometer. By knowing the specific refractive increment (the index change for a given concentration of molecules), the average biomolecular concentration can be directly inferred from the spectral shift of the peaks. Since many molecules are present, and each contributes to the refractive index, the measurement represents an average biomolecular concentration within the cell.

In accordance with this invention, the biomolecular concentration is used to assess the stages of the cell cycle and to identify possible failures in regulation of the cycle. During interphase, the cell must reproduce genetic material and the other protein components before it undergoes mitosis and cytokinesis (the final step in a cell splitting into two daughter cells). It is during this period that the cell is most active in transcribing and translating genetic information. There is no replication of DNA in the G1 phase, but in the S phase, the nucleus replicates its chromatin and cellular proteins. Thus the amount of DNA and protein must double. During G2 the cell is a resting phase before it proceeds to divide by mitosis. Most cells spend very little time in G2, so few cells would be found in this phase. On the other hand, irregular cell cycles induced by oncogenes or other perturbations alter the relative population of cells found in G1 and G2 phases. By measuring biomolecular concentration (or biomolecular mass in a fixed cell volume), it is possible to quantify the number of cells in G1 and G2 and assess the cell growth rate.

A cell grows by absorbing nutrients through the membrane from surrounding media. The uptake of biomolecular mass is thus proportional to the membrane area. On the other hand, the volume grows as the 3/2 power of the area. Thus the biomolecular concentration (mass over volume) must decrease as the inverse square root of the area during the initial growth of the cell. At some point, the cell volume must fix and then the biomolecular concentration can increase. The concentration increases significantly during synthesis phase because the DNA must replicate. During DNA replication it is likely that protein replication occurs almost simultaneously through normal transcription and translation. As a consequence, the concentration will approximately double as the cells enter G2. It is unlikely that the cell volume will increase significantly during synthesis, since this would necessitate a reduction in concentration and decrease replication rate. Only after mitosis when the genes are functional, would the cell volume be expected to increase.

Figure 3A:
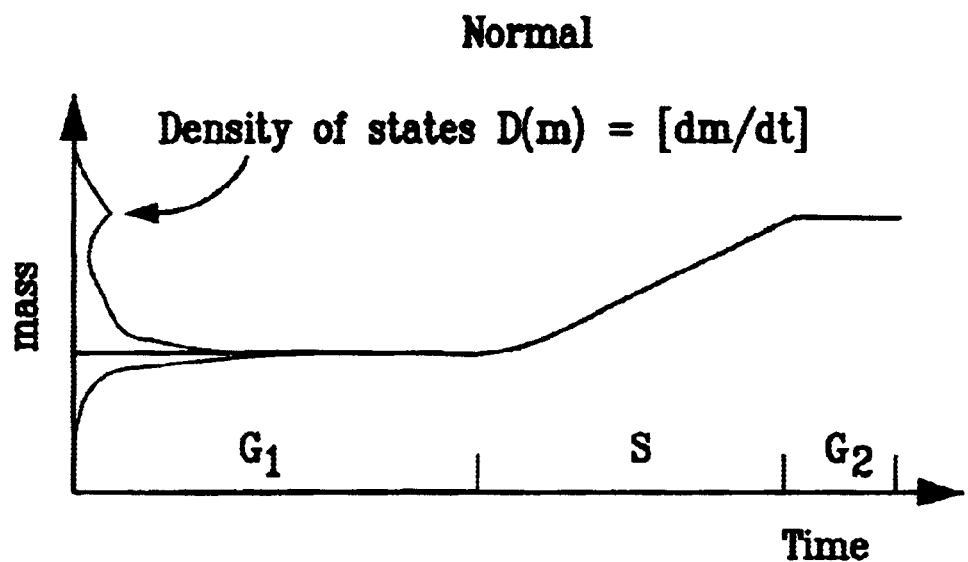
FIGS. 3A and 3B show the changes in mass of a normal and cancer cell during a cell cycle.
Figure 3B:
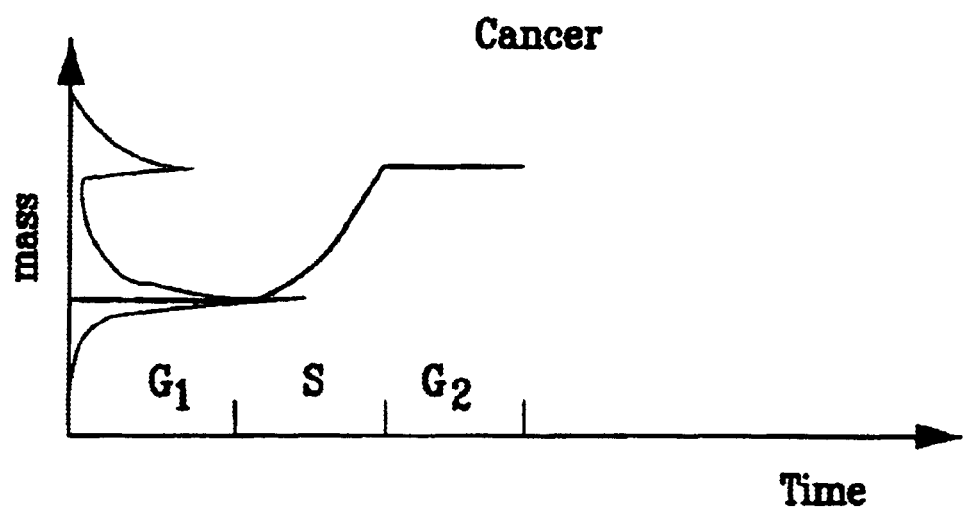

The wavelength shift measured by a biocavity laser indicates the difference in cell biomolecular concentration relative to the surrounding media, since it depends on the relative index of refraction of the cell and media. Thus this laser can track the changes in concentration during the cell cycle. The concentration c (or mass m for a fixed volume) is a function of time: c(t). The function must have the following characteristics illustrated in FIGS. 3A and 3B: it must start at a finite value $c_0$ after mitosis and growth slowly until time $T_1$ the end of G1. During synthesis c must increase abruptly before finalizing at approximately $2c_0$ at $T_1+T_S$. Then, c must be relatively constant for a time $T_2$ until mitosis. In a population of cells, the probability of finding a cell with a particular c will be inversely proportional to the dc/dt. So, the relative number of cells in G1 will be $T_1/\Delta c_1$ where $\Delta c_1$ is the small increase in c during G1. In S the number is $T_6/C_0$ and in G2 it is $T_2/\Delta c_2$. As shown in FIG. 3A, most of the cells are found in G1, and cells spend very little time in G2, so few cells are normally found here. However, as shown in FIG. 3B, oncogenes shorten $T_1$ and increase the number of cells in G2. These changes are observable with the biocavity laser. The curves along the vertical axis in FIG. 3 schematically represent the distribution of cells between the various phases of the cell cycle, as the cells increase in mass between G1 and G2 states. Mathematically, the probability of finding a cell in a given phase is approximately the inverse time derivative of the mass of the cell.

A first test of this invention has been undertaken with cultured astrocyte cells. Normal human astrocyte (NHA) cells are star-shaped process-bearing cells distributed throughout the central nervous system. NHA cells constitute from 20 to 50% of the volume of most brain areas and come in two forms: protoplasmic and fibrous types, predominant in gray and white matter, respectively. Some of these cells serve as scaffolding for the migration of neurons and play a critical role in defining the cytoarchitecture of the central nervous system.

Astrocytoma is a term given to tumors comprising astrocytes with a relatively well-differentiated histological appearance. Gliobastoma multiforme (GBM) is a term given to tumors which are the least differentiated and most aggressive form of astrocytoma. It accounts for about 20% of all primary intracranial tumor cases. The studies described herein used cultured normal human astrocytes from gray matter and glioblastoma cells as representative cells from normal and cancerous tissue, respectively.

Figure 4A:
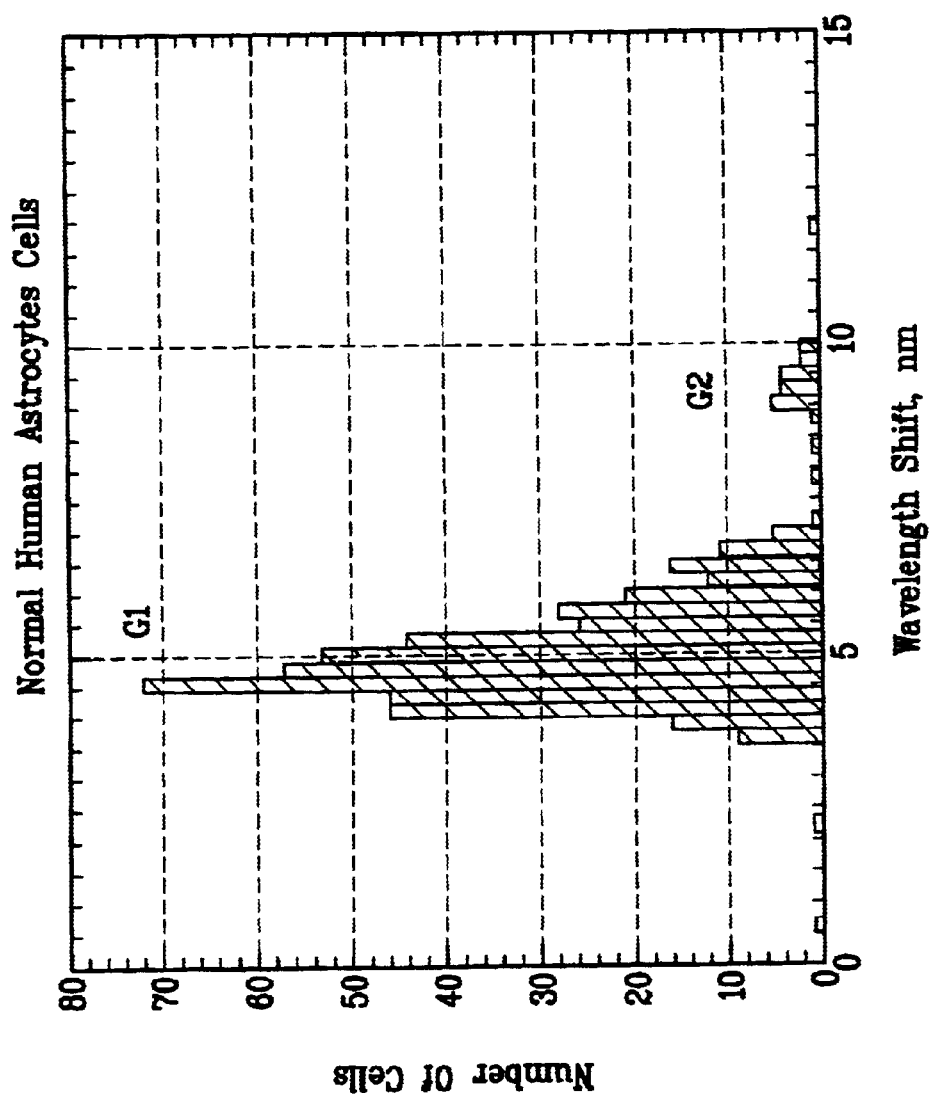
FIGS. 4A and 4B show histograms of spectral shifts in a biocavity laser for normal and cancer cells.

FIG. 4A shows a histogram of spectral shifts measured in a biocavity laser for a population of normal human astrocytes. The main peak near 4.5 nm represents cells in G1, comprising 98% of the population. The smaller peak near 9 nm represents the remaining 2% of cells in G2. This distribution of cells indicates that the cells are growing slowly (only 2% reach G2) with two well-defined population groups. This reproduction rate is consistent with normal cell replacement.

Figure 4B:
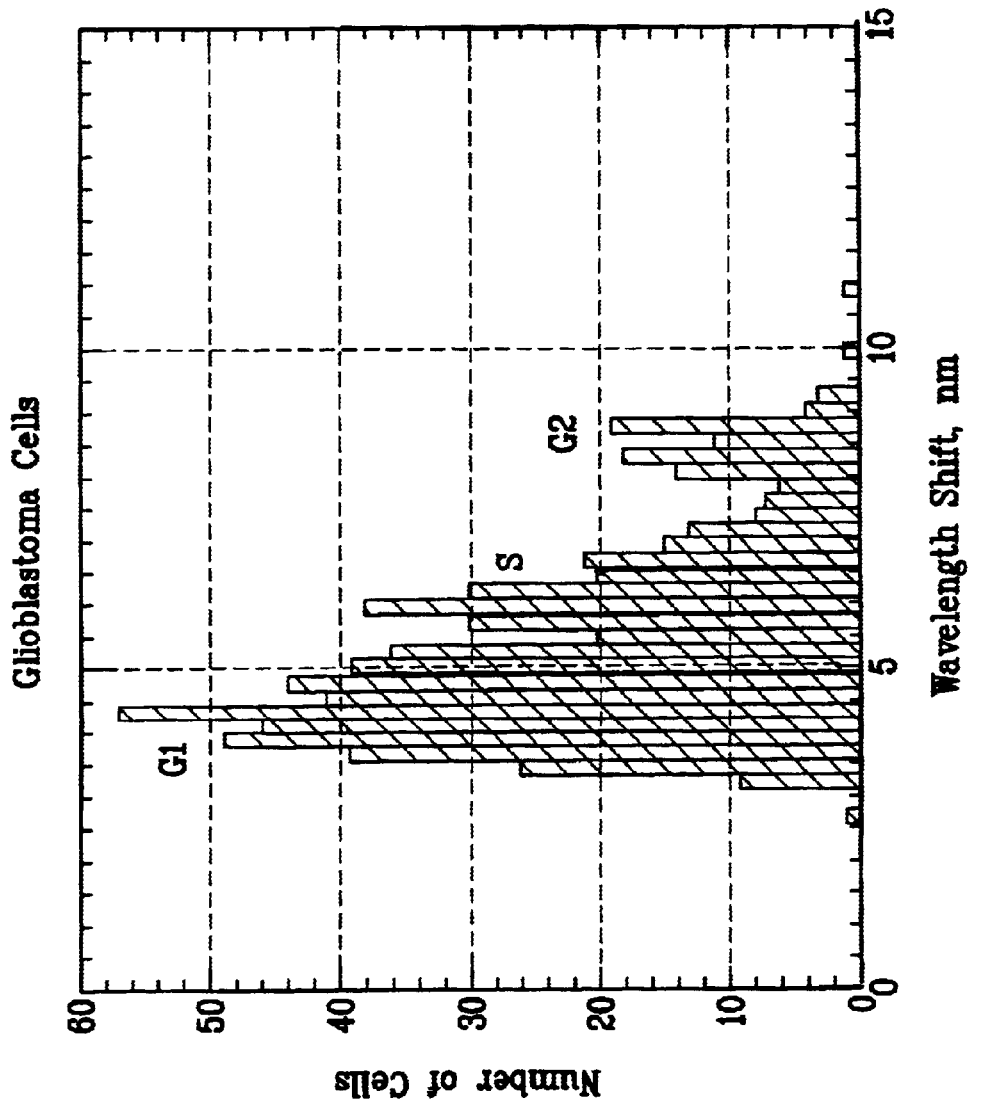

FIG. 4B shows test results for about 1000 glioblastoma cancer cells and reveal two subpopulations at 5 and 10 nm shifts corresponding to G1 and G2 phases. Here, there are considerably more cells (~5%) in the G2 phase. Further, the population is much more broadly distributed between the two phases, indicating many intermediate cells in the synthesis phase. These data indicate that the glioblastoma cells are proliferating at a much higher rate than the normal astrocytes, as expected for tumor cells. This observation is consistent with the measured rate of cell growth in culture and conventional flow cytometry data using protein markers in tumor cells.

Figure 2:
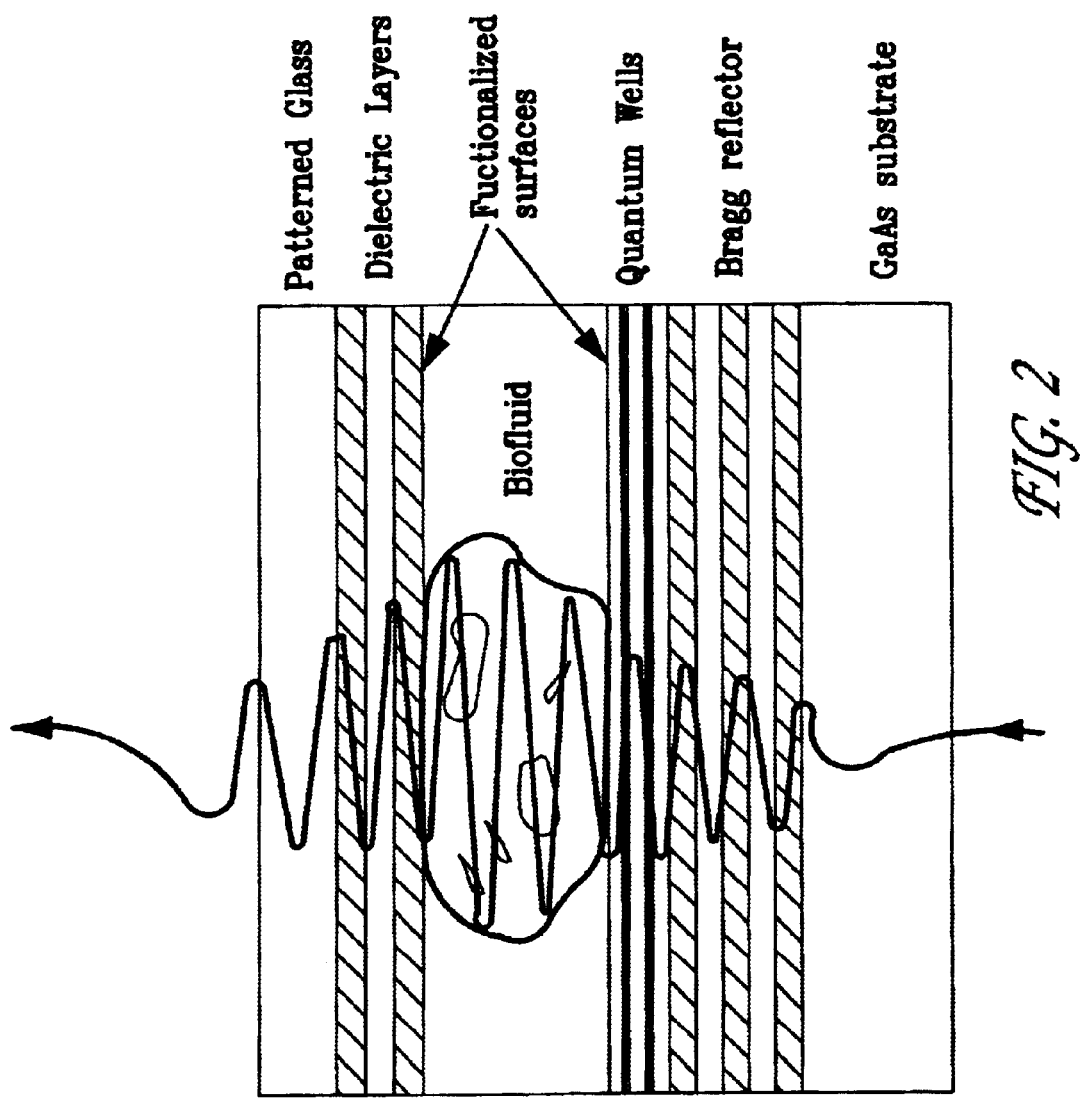
FIG. 2 shows a laser biocavity with a cell in accordance with the invention.
Figure 5A:
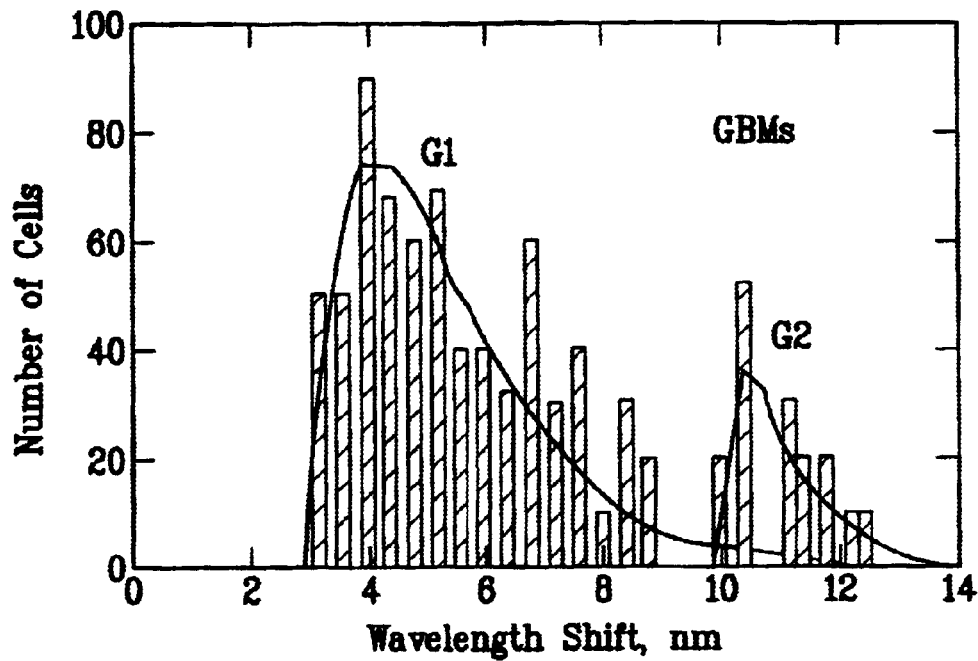
FIGS. 5A and 5B show histograms of spectral shifts of cancer cells and cancer cells in the G2 phase.
Figure 5B:
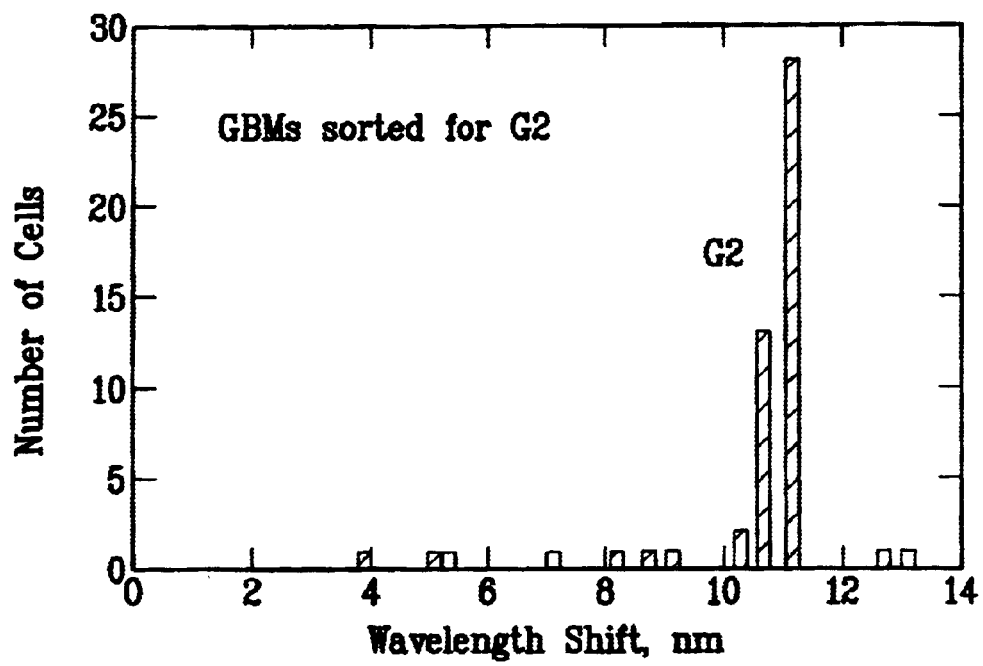

To check the identity of the G1 and G2 peaks, conventional flow cytometry was used to sort a mixed population of GBM cells into G2 cells. The unsorted and sorted cell suspensions were flowed through the microcavity of FIG. 2. FIG. 5A shows the unsorted suspension comprising G1 cells that exhibit a broad peak near 5 nm and G2 cells that exhibit a peak near 10 nm. FIG. 5B shows the corresponding histogram for the sorted G2 cells reveals only a single sharp peak near 10 nm. Thus, it is clear that the microcavity spectral peaks correspond to the G1 and G2 peaks observed with DNA tagging in conventional flow cytometry.

In FIG. 5A, the shape of the peaks has also been fitted with a theoretical function (solid line). The fitting function is the probability of finding a cell with a given biomolecular concentration c at a temperature T surrounded by a solution of concentration $c_0$. An osmotic pressure develops within the cell because the membrane acts as semipermeable barrier between the cytosol and the exterior. This pressure is given by $P=(c-c_0)kT$, which is the van't Hoff relation. The net energy to raise the concentration from $c_0$ to c against the diffusive force is PV where V is the cell volume. If an ensemble of cells was treated in analogy to a population of particles in thermal equilibrium, the chemical potentials of the cytosols of each cell would be equal to the chemical potential of the exterior solution. In this case the differential probability of finding a cell with energy E is proportional to $\exp(-E/kT)$. The probability distribution would take the form $f(\Delta c)\exp(-\Delta cV)$. The data was fitted to this functional form and found a best fit (solid line in FIG. 5A) of $\Delta c \exp(-\Delta cV)$, where $\Delta c$ is proportional to $\Delta\lambda$. This function features a sharp onset at low $\lambda$ and an exponential tail at high $\lambda$ as observed in the data of FIG. 5A.

Figure 6:
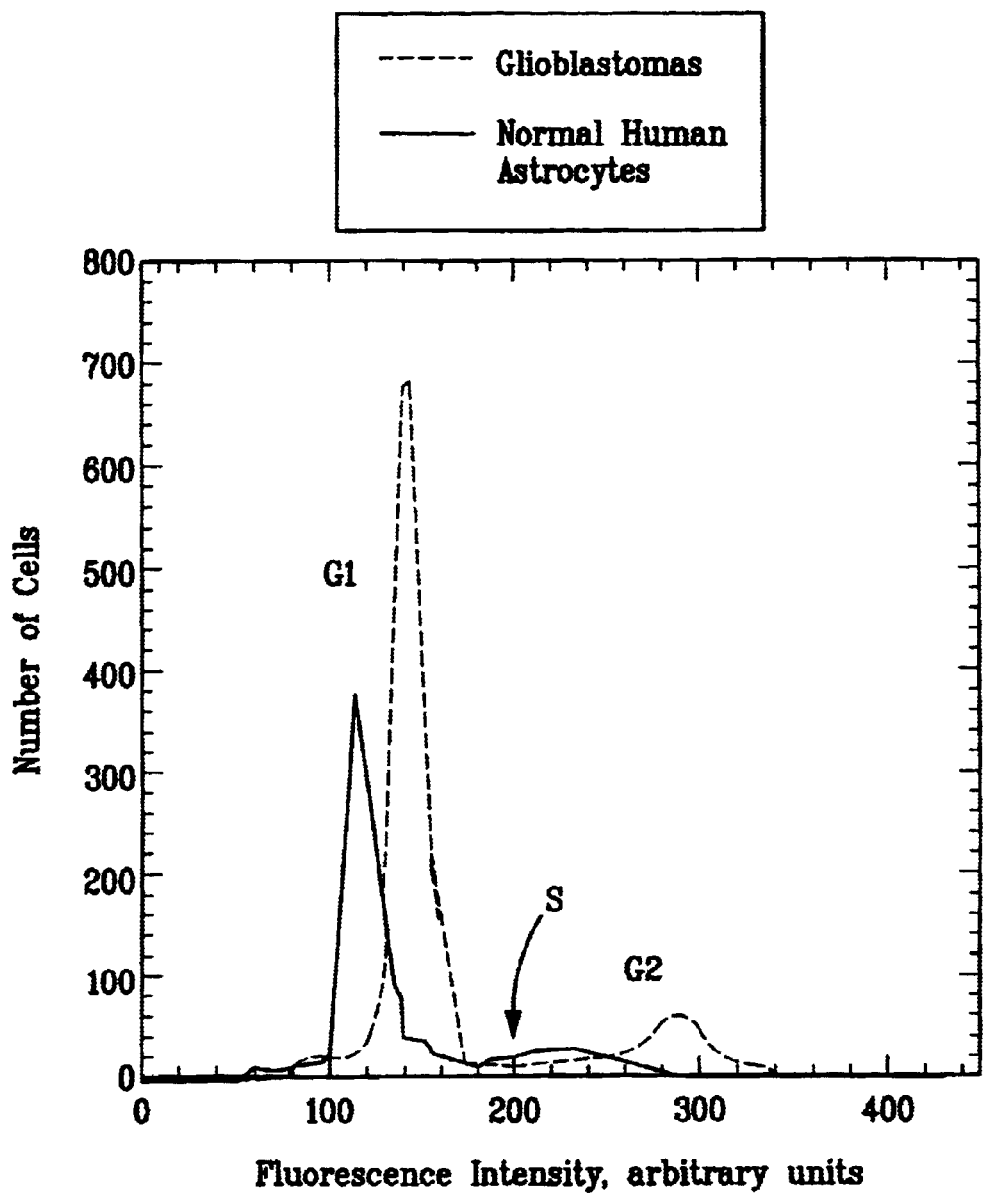
FIG. 6 shows a histogram of DNA fluorescence intensity for normal and cancer cells as measured by conventional flow cytometry.

FIG. 6 shows typical histograms of DNA fluorescent intensity recorded by conventional flow cytometry with normal human astrocytes (dashed lines) and glioblastoma cells (solid lines). Both curves reveal major G1 subpopulations and minor G2 subpopulations. The intensities of the G2 peaks are exactly double the intensities of the G1 peaks for a given cell type. This is expected if the synthesis process exactly replicates the DNA. However, the ratio G2/G1 increases for GBM cells as expected for enhanced replication rate. Also, the amount of DNA is increased by some 15% in the GBM cells, probably due to extra DNA arising from mutated replication. These observations of DNA content are similar to the data obtained with the biocavity laser for total biomolecular concentration (primarily protein), except that the protein content appears about 15% smaller in the GBM case.

DNA is believed to have a lower refractive index relative to other cellular constituents such as major proteins. Thus, the greater DNA content in the GBM cells (shown in FIG. 6) should result in a lower wavelength shift of the cell mode than a normal cell, as verified by the results in FIGS. 4A and 4B, where normal G2 cells are seen to have shifted about 9 nm and GBM G2 cells have shifted about 8 nm.

It is noted that the shift of the G2 peak for the GBM cells of FIG. 4B is 8 nm, while the shift for the G2 GMB cells in FIG. 5A is 10 nm. This difference is an experimental artifact due to slight differences in the particular microcavity used for the experiment, and can easily be eliminated by employing cavities made more uniformly by precise manufacturing processes. However, the number of G2 cells is easily determined from either measurement.

It remains an open question if the total biomolecular content measurement of a biocavity laser is able to detect cancer in an individual cell. Such a measurement would have to detect differences in the cells that are unique to cancerous cells. However, as a practical point, it is also very difficult to isolate a single cell for measurement in a medical environment. This invention provides a determination from a few hundred cells in a nanoliter of material, a very small volume easily moved by syringe to a test device, or examined by a test device on a probe that is applied directly to the patient. Thus, a surgeon could test cells as they are removed from the patient to quickly determine if an entire tumor has been removed.

The particular test discussed above is cited merely to illustrate a particular embodiment of this invention. It is contemplated that the use of the invention may involve many types of cancerous cells as long as the principle, using a biocavity laser to determine an increase in the percentage of G2 cells, is followed. Many techniques may be used to process the information from the biocavity. For example, after a predetermined number of cells are tested, the number of cells that fall within a wavelength shift range where G2 cells are expected could be provided. Alternatively, histograms such as described herein could be plotted. It is intended that the scope of the invention be defined by the claims appended hereto.

What is claimed is:

1. A method of determining a rate of cell reproduction using a laser biocavity including a semiconductor laser, comprising:

a) determining a laser wavelength of a laser biocavity;

b) determining a wavelength shift of the laser wavelength of the laser biocavity when a cell in a fluid passes through a microchannel of the laser biocavity;

c) categorizing a phase of the cell by comparing the wavelength shift of the laser wavelength of the laser biocavity to a wavelength shift generated by a G2 phase call of the same type as the cell in the fluid to determine whether the cell is in a G2 phase;

d) determining the phase of a plurality of cells by repeating steps b and c; and e) determining a percentage of the plurality of cells in a G2 phase as an indication of the rate of cell reproduction.

2. The method of claim 1 wherein the step of determining the percentage of the plurality of cells comprises counting a total number of the cells which have passed through the microchannel and counting a number of the cells which have passed through the microchannel that produce a wavelength shift corresponding to the laser wavelength of the laser biocavity containing a cell in the G2 phase.

3. The method of claim 1 wherein the step of determining the percentage of the plurality of cells in a G2 phase comprises forming a histogram of a number of the cells as a function of the wavelength shift produced by each of the cells, and comparing a number of cells at a wavelength shift corresponding to the laser wavelength of the laser biocavity containing the cells in the G2 phase with a number of cells at a wavelength shift corresponding to the laser wavelength of the laser biocavity containing the cells in the G1 phase.

* * * * *